(12) United States Patent
Roreger

(10) Patent No.: US 6,761,908 B1
(45) Date of Patent: Jul. 13, 2004

(54) COLLAGEN PREPARATION FOR THE CONTROLLED RELEASE OF ACTIVE SUBSTANCES

(75) Inventor: Michael Roreger, Neuwied (DE)

(73) Assignee: Lohmann & Rauscher GmbH & Co., KG, Rengsdorf (DE)

(*) Notice: Subject to any disclaimer, the term of this patent is extended or adjusted under 35 U.S.C. 154(b) by 0 days.

(21) Appl. No.: 08/737,111

(22) PCT Filed: Apr. 15, 1995

(86) PCT No.: PCT/EP95/01428

§ 371 (c)(1),
(2), (4) Date: Oct. 25, 1996

(87) PCT Pub. No.: WO95/28964

PCT Pub. Date: Nov. 2, 1995

(30) Foreign Application Priority Data

Apr. 27, 1994 (DE) .......................... 44 14 755

(51) Int. Cl.⁷ ............................ A61K 9/10; A61K 9/20; A61K 9/16; A61K 47/42; A61L 15/32
(52) U.S. Cl. ...................... 424/484; 424/499; 424/464; 424/444; 424/426; 424/428; 424/45
(58) Field of Search ................................ 424/484, 499, 424/464, 465, 443, 444, 447, 422, 423, 426, 428, 45

(56) References Cited

U.S. PATENT DOCUMENTS

| | | | |
|---|---|---|---|
| 4,021,522 A | 5/1977 | Daniel | 264/138 |
| 4,279,812 A | * 7/1981 | Cioca | |
| 4,409,332 A | 10/1983 | Jefferies et al. | 435/188 |
| 4,563,350 A | 1/1986 | Nathan et al. | 424/95 |
| 4,619,913 A | 10/1986 | Luck et al. | 514/2 |
| 4,774,091 A | 9/1988 | Yamahira et al. | 424/426 |
| 4,789,663 A | 12/1988 | Wallace et al. | 514/21 |
| 5,024,841 A | 6/1991 | Chu et al. | 424/422 |
| 5,206,028 A | 4/1993 | Li | 424/484 |
| 5,246,457 A | 9/1993 | Piez et al. | 623/16 |

FOREIGN PATENT DOCUMENTS

| | | |
|---|---|---|
| DE | 2 719 770 | 12/1977 |
| DE | 2 716 602 | 2/1978 |
| DE | 2 843 963 | 4/1980 |
| DE | 3 034 273 | 4/1981 |
| DE | 3 429 038 | 2/1986 |
| DE | 3 841 397 | 6/1990 |
| EP | 0 224 453 | 6/1987 |
| EP | 0 304 374 | 2/1989 |
| EP | 0 429 438 | 5/1991 |
| EP | 0 518 697 | 12/1992 |
| EP | 0 567 234 | 10/1993 |
| WO | WO85/04413 | 10/1985 |
| WO | WO93/00890 | 1/1993 |

* cited by examiner

Primary Examiner—Edward J. Webman
(74) Attorney, Agent, or Firm—Wenderoth, Lind & Ponack, L.L.P.

(57) ABSTRACT

A collagen preparation for the controlled release of active substances is characterized in that it has mixtures of acid-insoluble collagens with different molecular weight distributions.

15 Claims, No Drawings

COLLAGEN PREPARATION FOR THE CONTROLLED RELEASE OF ACTIVE SUBSTANCES

A number of polymers are used in the production of administration forms for pharmaceutical or cosmetic active substances. Depending on the site of application, these are used to impart to the respective administration form the desired properties. Agents for the treatment of wounds and implantable materials should be adapted to the surface of the respective application site, and they should not interfere with the function and activity of body cells, such as keratinocytes, fibroblasts, or endothelial cells. In these cases the spectrum of suitable polymers is therefore limited to those having an excellent compatibility on contact with connective tissue and which preferably are biodegradable.

For quite a long time now, collagen, the main protein of the connective tissue, has gained a special place among the polymers suitable for this purpose. This is due to the biological compatibility and degradability of the administration forms produced therefrom. Such collagen preparations are for the most part used as wound dressings without any additional additives. However, there have also been attempts to charge collagen matrices of most different kinds with biologically active substances and to influence the release of these substances, which in general follows the dissolution and/or enzymatic degradation of the collagen carrier matrix, by the kind, structure and composition of the matrix.

To produce collagen matrices—such as those described in, for example, U.S. Pat. No. 5,024,841, U.S. Pat. No. 4,789,663, U.S. Pat. No. 4,774,091, U.S. Pat. No. 4,563,350 U.S. Pat. No. 5,246,457, or EP 429 438—solutions of telopeptide-free, acid-soluble collagen are used in general. These are used to obtain reconstituted fibrils by means of dialysis, shift of the pH, or other processes; and these fibrils are then processed by means of different methods into preferably porous matrices. These preparations can exhibit an excellent biocompatibility since they consist of pure collagen, but they have the disadvantage that a retardation of the active substance release is limited owing to the use of soluble collagen.

Such a release retardation can be achieved by decreasing the solubility of the collagen matrix by using cross-linking agents or binders, as is described, for example in U.S. Pat. No. 4,409,332, DE 2 843 963, WO 93/00890, or WO 85/04413, or by using coating agents, e.g., described in DE 38 41 397, or by combining water-soluble collagen with other polymers, preferably natural anionic polymers or their derivatives. However, owing to the additional components, additional toxicological risks which, in particular when the known cross-linking agents for collagen are used, should not be underestimated must be accepted in each of these cases.

Another possibility of delaying the active substance release is described in EP 518 697. Here, laminates are produced from water-soluble and/or water-insoluble collagen, which consist of one or several active substance-containing reservoir layers and one layer retarding the active substance supply. As compared to the above-mentioned preparations, a retardation of the release while minimizing the toxicological risks could be achieved with such laminates. However, they have the disadvantage that their production is extremely expensive and that the adherence of the layers can only be achieved with "moist" films. Dry films which are absolutely necessary in case of active substances susceptible to decomposition cannot be joined to form such laminates, for example.

However, a retardation of the active substance release is not always desired. EP 224 453 describes a collagen matrix which mainly consists of water-insoluble, reticulated collagen and additionally comprises water-soluble, non-reticulated collagen. In cosmetic preparations, e.g., face packs, said soluble collagen serves as active substance which, after application, is dissolved out by means of the natural cutaneous moisture or by extremely moistening the preparation which then takes effect on the skin. For pharmaceutical purposes, active substances can be incorporated into the preparation, these are then dissolved out and released from the collagen matrix together with the soluble collagen very quickly after application. Such a collagen preparation can be useful in cases where a rapid release is desired and appropriate.

Mechanisms to delay or accelerate the active substance release from collagen preparations have been described in many ways. However, due to the given composition, each of these prior art collagen preparations offers only one possibility of influencing the release, and therefore they have a given release profile each tailor-made to one specific problem, e.g., a certain active substance or certain active substance group, a certain therapeutic principle, or a certain disease. None of the prior art collagen preparations can achieve a selective and at the same time manifold control of the active substance release, i.e., permit a variable and individual adaptation of the release kinetics of active substances to differing problems, wherein factors, such as different active substance properties and differences in the onset and duration of action, can be considered adequately for each case.

Accordingly, it was the object of the present invention of find a collagen preparation which is not only suitable for a certain active substance, a certain active substance combination, or a certain release profile, but also permits—for a great variety of uses—a wide-ranging, reliable control of the active substance release adapted to the respective problem.

Most surprisingly, the solution of this object has been found in a collagen preparation for the controlled release of active substances, comprising mixtures of acid-insoluble collagens having different molecular weight distributions.

According to one embodiment, the collagen preparation comprises different active substances. It may additionally comprise adjuvants, such as viscosity regulators, binders, humectants, softening agents, penetration enhancers, preservatives, disinfectants, pH-regulators, antioxidants, active substance stabilizers, oils, fats, waxes, emulsion stabilizers, odorous substances, dyes, and/or inert fillers.

According to a preferred embodiment, the insoluble collagen is telopeptide-free, native, uncross-linked Type-1-collagen. This may be an insoluble collagen which is a product obtained from calfskin by means of alkaline decomposition.

Furthermore, the collagen preparation may be present in the form of powders, dusts, microparticles, fibers, flakes, foams, sponges, needles, small rods, tablets, gels, creams, single-layer films, or laminates.

Advantageously, the collagen preparation may include combinations of different administration forms to achieve the desired release kinetics.

It is preferred that the collagen preparation be bioadhesive.

A process for the production of the collagen preparation may comprise spray drying, freeze-drying, coating or casting with subsequent drying, phase separation and coacervation processes, compression, or filling into containers.

According to the process, the active substance release can additionally be influenced and/or controlled by the mixing ratio of acid-insoluble collagens with different molecular weight distributions. According to the process, the active substance release can additionally be controlled by dissolution, swelling, or erosion of the collagen preparation. Another possibility of controlling the active substance release is by biological degradation of the collagen preparation.

The use of the collagen preparation according to the present invention consists in the controlled release of the active substance to wounds. However, the use may also be directed to the controlled release of active substances to intact skin. Finally, the use of the collagen preparation may serve to implant or inject active substances into a living organism.

In general, prior art collagen preparations for the active substance release are produced from acid-soluble collagen, that is collagen which is dissolved clearly in dilute acids at a pH of 2. This acid-soluble collagen can be isolated from several animal and vegetable tissues by means of a great variety of processes.

In contrast to this, the collagen used according to the present invention is an acid-insoluble collagen which—when it is present in aqueous dispersion—cannot be brought into solution even when concentrated acetic acid is added.

It is preferred that this insoluble collagen be native collagen the greater part of which Is present as Type-I-collagen and the smaller part as Type-III-collagen. The term native collagen refers to a collagen molecule having an unchanged triple-helical tertiary structure.

The insoluble collagen used according to the present invention can be obtained from biomaterial of various origins by alkaline decomposition; for this purpose processes, such as those described, for example, in DE-OS 3034273, U.S. Pat. No. 4,021,522, or DE-OS 27 16 602 are slightly modified. It is preferred that the starting material be calfskin, aged for six months. In contrast to the normally used tissues and body parts of cattle, pigs, or horses, this ensures a starting material of a defined, constant quality, this in turn ensuring the reliable reproducibility of the process steps described in the following and illustrated in greater detail in Example 1 hereunder.

First, the calfskin is mechanically dehaired and degreased. Then, soluble collagens and non-collagenous soluble components of the connective tissue are extracted and rejected. Next, the connective tissue is first treated with an aqueous solution of an alkali hydroxide, preferably sodium hydroxide, and an alkali sulfate, preferably sodium sulfate, and then with an aqueous alkali sulfate solution to saponify and dissolve out sebaceous matter and to swell the collagen fibers in a controlled manner. When this is done, the terminal, non-helical portions of the collagen molecule, the so-called telopeptides which are mainly responsible for the antigenic properties of xenogeneic collagen, are also split off. In addition, the treatment with alkali hydroxide/alkali sulfate solution and with pure alkali sulfate solution splits a defined portion of the intermolecular collagen bonds in the fiber composite of the swollen connective tissue, said portion depending on the concentration and the duration of action of the solutions. The intramolecular bonds of the collagen are not attacked so that the helical structure of the molecule remains undamaged. The connective tissue so decomposed is washed out with water and dilute acids in several stages, purified and neutralized, and then mechanically comminuted and dispersed in water.

The decisive step for the isolation of the acid-insoluble collagen having different molecular weight distributions used according to the present invention is the selective alkaline cleavage of the intermolecular collagen bonds. If, for example, an aqueous solution of 9.75% sodium hydroxide and 9.2% sodium sulfate is allowed to react on the swollen connective tissue for 48 hours, the HPLC-analysis (column system Biosil TSK-400+Biosil TSK-125; eluent 0.5 m ammonium acetate buffer pH 6.7; detector UV 275 nm; sensitivity range 0.02 AUFS) with assessment against standard-protein chromatograms shows an average molecular weight of about 420,000 for the insoluble collagen after dispersion in water. In contrast to this, if the swollen connective tissue is treated with an aqueous solution of only 5% sodium hydroxide and 9.2% sodium sulfate for only 12 hours, far fewer intermolecular bonds are split, and the analysis of the insoluble molecular aggregates obtained after dispersion in water shows a mean molecular weight of about 2,500,000. These differences first of all affect the flow behavior and with that the processability of the dispersions of insoluble collagen. Whereas a dispersion with 5% of low-molecular, insoluble collagen is a viscous but still free flowing mass, the flow limit of a dispersion of higher-molecular, insoluble collagen is at about 2.5%.

Thus, the variable factors of the decomposition process, by variation of which different molecular weight distributions can be achieved each time, are concentration and reaction time of sodium hydroxide. The higher the concentration of sodium hydroxide and/or the longer its duration of action, the lower the mean molecular weight of the isolated, acid-insoluble collagen, and vice versa. To represent the connection between the molecular weight that can be achieved and the described decomposition conditions, e.g., in the form of a curve, one of the influencing factors, i.e., concentration or duration of action, would have to be kept constant while the other one is changed. This is possible in principle, but from the production and operational point of view this is rather useless, since, for example, a free variation of the duration of action alone is not possible in general. For instance, very long reaction times with a correspondingly low sodium hydroxide concentration would increase both the machine running times and the requirement of personal; in view of the operating expenses this is not acceptable. On the other hand, owing to the required higher sodium hydroxide concentration, very short durations of action result in increased wear of the manufacturing facilities, e.g., of the conduits and filtering installation, and this cannot be realized either because of increasing working expenses. Therefore, the required duration of action and concentration of sodium hydroxide must individually be ascertained empirically for each problem in such as manner that they represent an optimum both with respect to the demands on the administration form, in particular regarding the release kinetics of the active substance, and to economic efficiency.

The differences in the molecular weight distribution of insoluble collagen distinctly influence the properties of the collagen preparations that are produced therefrom by means of drying. Example 2 shows that, depending on the mixing ratio, foams of insoluble collagen with different molecular weight distributions produced by means of freeze-drying have very different disintegration properties. While foams consisting of 100% of low-molecular, insoluble collagen completely decompose in artificial wound exudation of pH 6.4 after only 45 minutes, foams made of 100% of higher-molecular, insoluble collagen have not disintegrated even after 10 days under the same conditions.

The example shows that the use of high-molecular collagen aggregates has a clearly stabilizing effect on the foam;

this is expressed in a clearly slowed down absorption of secretion and swelling, and in a very delayed disintegration. Form stabilization by means of maintaining a high natural cross-linking degree of the collagen has the important advantage, in particular from the toxicological point of view, that no additional manipulations to consolidate the structure, e.g., by tanning or cross-linking, are required. The product is rendered dimensionally stable by merely maintaining the collagen's original quaternary structure, such as that present in the skin, to a substantial degree.

Thus, the collagen foams, each manufactured from only one single basic type of insoluble collagen, show clear differences, for example, with respect to interaction with the secretion of the wound. However, as mentioned above, the profile which is required for a collagen product and is based on a specific purpose can only in special cases be satisfied by such mono-preparations. Compared with that, the present invention offers two possibilities of exactly tailoring the properties of a collagen preparation to given demands on a product. On the one hand, the molecular weight distribution of the insoluble collagen can continuously be varied over a very wide range by selectively controlling the cleavage of the intermolecular bonds. On the other hand, the required product properties can be adjusted by mixing said variations of insoluble collagen each having different molecular weight distributions. If the already mentioned Example 2 is continued, this becomes clear, for instance, by the disintegration of freeze-dried foams, where—prior to drying—insoluble collagen having a mean molecular weight of about 420,000 and insoluble collagen having a mean molecular weight of about 2,500,000 were mixed at always different ratios. With different pH-values, the decay periods always show a gradual decrease when the percentage of insoluble collagen having a low average molecular weight is gradually increased.

The exact adjustment of the product properties to a demand profile representing the optimum for the respective therapy is of importance primarily in the therapy using pharmaceutical active substances.

Since the collagen preparation according to the present invention is preferably used on the skin, on external and internal wounds, and in internal body tissues and body cavities after implantation or injection, the active substances suitable for charging the collagen preparation preferably are active substances for the dermal and transdermal application, active substances for the treatment of wounds and for the promotion of wound-healing, as well as active substances usually administered by means of preparations for implantation or injection.

For the dermal treatment of local skin diseases the following substances are used: local anaesthetics, local antibiotics, antiseptics, antimycotics, antihistaminics, and antipruritic drugs; keratolytics and caustic drugs; virustatics, antiscabietic agents, steroids, as well as different substances for the treatment of acne, psoriasis, or photodermatoses. Active substances applied intradermally include, for example, steroid and non-steroid antirheumatics, substances stimulating the blood flow, or vasoprotectors and vaso constrictors for the treatment of vascular diseases. The active substances applied transdermally include, for example, neuroleptics, antidepressants, tranquilizers, hypnotics, psychostimulants, analgesics, muscle relaxants, antiparkinson drugs, ganglionic blockers, sympathomimetics, alpha-sympatholytics, beta-sympatholytics, antisympathotonics, antidiabetics, coronary therapeutic agents, antihypertensives, anti-asthmatics, or diuretics. The collagen preparation according to the present invention can also be used on the skin in cosmetic preparations, e.g., in the form of lather masks or films for the treatment of, for example, aged skin, wrinkles, or impure skin; for body care, depilation, reduction of perspiration, or for light protection.

Active substances which are used in the collagen preparations according to the present invention on external and internal wounds, preferably are styptic active substances, among which collagen itself has a special place; wound-cleansing substances, such as enzymes, antiseptics, disinfectants, and antibiotics; as well as active substances promoting wound healing which stimulate granulation, induce vascularization, or promote epithelization. Among the active substances promoting the wound healing, biologically active peptides and proteins—which develop high activities at only very low concentrations and are mainly manufactured by recombinant technologies—increasingly gain importance. The collagen preparation according to the present invention represents a particularly suitable carrier and release system for these substances which include the so-called growth factors, such as Platelet derived growth factor (PDGF), Epidermal growth factor (EGF), Platelet derived endothelial cell growth factor (PD-ECGF), acidic Fibroblast growth factor (aFGF), basic Fibroblast growth factor (bFGF), Transforming growth factor α (TGF α), Transforming growth factor β (TGF β), Keratinocyte growth factor (KGF), Insulin-like growth factors 1 and 2 (IGF1, IGF2), and Tumor necrosis factor (TNF).

The active substances administered parenterally by means of the collagen preparation according to the present invention include, for example, antibiotics, antiseptics, anaesthetics, analgesics of varying strengths; cytostatics, hormones, steroids, cytokinins, such as interleukins, interferons, and colony-stimulating factors, Hormone releasing and release inhibiting factors, prostaglandins, enzymes, as well as growth factors, in particular osteoinductively effective bony growth factors.

One of the greatest challenges for the development of active substance-containing preparations is to find formulations releasing the active substance in such a manner that the optimum action and best therapy is achieved. The half-life period of many active substances, in particular of the above-mentioned biologically active peptides and proteins, in the body is relatively short, and for this reason they must frequently be administered several times a day.

Therefore, active substance vehicles releasing the active substances in a delayed or even controlled manner gain increasing importance. Collagen preparations according to the present invention offer the possibility of developing carrier systems using relatively few formulation base components. These systems are very flexible both with regard to application and design, and can exactly be directed to the required solution of a problem. The mechanisms, which impart to the release kinetics of an active substance its characteristic features, can selectively be controlled by mixing of insoluble collagen having different molecular weights and by shaping of the collagen preparation. These factors, in addition to structure and density of the polymeric collagen skeleton, also influence the number and distribution of hydrophilic, hydrophobic and ionic bonds along the polymer skeleton. Since active substance can not only be enclosed in cavities of a collagen preparation according to the present invention, but can also be adsorbed to the surface of the collagen skeleton, the bonding force between collagen and active substance—and thus its release behavior—is substantially-determined by ionic relations as well as by hydrophilic and hydrophobic interactions.

In the dermal, intradermal and transdermal application of an active substance using a collagen preparation according to the present invention, the solubility of the active substance in the preparation, the degree of charge and saturation, and the diffusion rate of active substance within the preparation—in addition to structure, density and bonding activity of the collagen preparation—have an influence on the release behavior.

In case of collagen preparations for the release of active substances to external or internal wounds and collagen preparations for implantation or injection another factor appears.

Since the collagen preparations according to the present invention come into contact with body fluid in the applications mentioned above, the rate and amount of liquid absorbed by the collagen preparation and consequently the swelling capacity and disintegration properties of the collagen preparation can be used to control the release, as is shown in Example 2 mentioned hereinbefore. In addition to the decay of the collagen preparation used as controlling mechanism, other suitable mechanisms with regard to the release control on contact with body fluid primarily include the dissolution of active substance out of the collagen preparation by means of body fluid and the fluid-induced diffusion of active substance from the center of the collagen preparation to its interface. Furthermore, the release is influenced by the biological degradation of the collagen preparation by means of hydrolysis and enzymatic reaction on contact with body fluid. The wide range of interaction between the liquid and preparations of mixtures of insoluble collagen having different molecular weight distributions has already been shown in Example 2. The way said interactions in combination with one or several of the above-mentioned influencing factors take effect on the release kinetics of an active substance is illustrated Examples 3 and 4. It is made clear that the mixing ratio of insoluble collagen having different molecular weight distributions significantly influences the kinetics of the active substance release. In the case of a given active substance and a given desired release per time unit, it is thus possible to adapt the collagen preparation selectively to the required demands; in this way an optimum active substance dosage for the respective therapy is achieved after application over the pre-determined application period. If active substance is to be released over an application period of 24 to 48 hours from the administration form chosen in Examples 3 and 4—manufactured of the preparations of insoluble collagen having different molecular weight distributions as described in Example 1—the mixing ratio of low-molecular and high-molecular insoluble collagen should not be lower than 3 to 1. If, on the other hand, an even, delaying active substance release from a comparable administration form is to take place over an application period of 7 to 14 days, the mixing ratio of low-molecular and high-molecular insoluble collagen should not be greater than 1 to 3.

In order to prove the controlling possibilities of preparations consisting of mixtures of insoluble collagen having different molecular weight distributions, free from any influence of other auxiliary agents, pure collagen preparations plus active substance were exclusively used in the Examples on purpose. In practice, however, it will not be possible to do without additional water-soluble or water-dispersible additives, since, in addition to the requirements regarding the active substance release, the intended purpose will usually also result in demands with respect to handling properties and stability of an active substance-collagen-preparation.

Such adjuvants may be additional polymers, e.g., serving as viscosity regulators when liquid preparations are used or as binders when solid forms are used, for example, cellulose derivatives, starch derivatives, galactomannan derivatives, dextrans; vegetable polysaccharides, such as alginates, pectins, carrageenan, or xanthan, chitosan, proteins, glycoproteins, proteoglycans, glucosaminoglycans, polyvinyl alcohol, polyvinylpyrrolidone, vinyl pyrrolidone-vinyl acetate copolymers, polyethylene glycol, polyacrylates and polymethacrylates, polylactides and polyglycolides, as well as polyamino acids.

The collagen preparation may comprise as additional adjuvants:

humectants, such as glycerol, sorbitol, polyethylene glycol, polypropylene glycol, softening agents, such as citric acid ester, tartaric acid ester, or glycerol ester, penetration enhancers, such as alkyl sulfates, alkyl sulfonates, alkali soaps, fatty acid salts of multivalent metals, betaines, amine oxides, fatty acid esters, mono-, di- or triglycerides, long-chain alcohols, sulfoxides, nicotinic acid ester, salicylic acid, N-methyl pyrrolidone, 2-pyrrolidone, or urea, preservatives, such as p-Cl-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or digluconate, ethanol, or propylene glycol.

Disinfectants, for example, halogens, such as polyvidoneiodine; halogen compounds, such as sodium hypochloride or tosylchloride sodium; oxidants, such as hydrogen peroxide or potassium permanganate; aryl mercury compounds, such as phenylmercury borate or merbromin; alkyl mercury compounds, such as thiomersal; organotin compounds, such as tri-n-butyltin benzoate; silverwhite compounds, such as silverwhite acetyltannate; alcohols, such as ethanol, n-propanol, or isopropanol; phenols, such as thymol, o-phenylphenol, 2-benzyl-4-chlorophenol, hexachlorophene, or hexylresorcinol; or organic nitrogen compounds, such as 8-hydroxyquinoline, chloroquinaldol, clioquinol, ethacridine, hexetidine, chlorohexidine, or ambazone.

pH-regulators, such as glycerol buffers, citrate buffers, borate buffers, phosphate buffers, or citric acid phosphate buffers.

Antioxidants, such as ascorbic acid, ascorbyl palmitate, tocopherol acetate, propyl gallate, butylhydroxyanisole, or butylated hydroxytoluene.

Active substance stabilizers, such as mannitol, glucose, lactose, fructose, saccharose, emulsifyable inactive ingredients, such as oils, fats, and waxes, odorous substances, dyes, cleaning agents, substances for personal hygiene, emulsion stabilizers, such as non-ionogenic emulsifiers, amphoteric emulsifiers, cation-active emulsifiers, and anion-active emulsifiers, fillers, such as micro-crystalline cellulose, aluminum oxide, zinc oxide, titanium oxide, talcum, silicon dioxide, magnesium silicate, magnesium aluminum silicate, kaolin, hydrophobic starch, calcium stearate, or calcium phosphate.

For example, adjuvants may be dissolved, dispersed, or emulsified in dispersions of insoluble collagen prior to shaping the administration form. However, they may also be introduced in a manner usual and known for the respective shaping processes after termination of a primary forming process (described hereinafter) of the mixtures of insoluble collagen during later stages of the drug shaping.

The embodiments wherein admixtures of insoluble collagen of different molecular weight distributions may be used for the controlled release of active substances are so numerous and manifold that they cannot be represented herein extensively.

These embodiments of the collagen preparation according to the present invention may be manufactured from mixtures of dispersions of insoluble collagen each having different molecular weight distributions according to various methods known to the skilled artisan; for example by spray drying, freeze-drying, coating or casting with subsequent drying, phase separation and coacervation processes for particles or emulsified droplets, drying and compression, as well as by simple filling into containers, e.g., tubes. They result in, for example, powders, dusts, microparticles, fibers, flakes, foams, sponges, needles, small rods, tablets, gels, creams, single-layer films, or laminates. Preferred embodiments are spraydried microparticles, freeze-dried foams, and gel-like films manufactured by coating.

The introduction of active substance into the collagen preparation according to the present invention may be effected such that the active substance is dissolved or dispersed in the finished mixture of dispersions of insoluble collagen having different molecular weight distributions, prior to forming the preparation. If more than one active substance is to be incorporated, these may also be dissolved or dispersed separately from one other in the individual fractions of insoluble collagen, prior to the mixing process. Active substance may also be introduced on or into the preparation after the shaping process of the preparation by means of coating, spraying, impregnating, dipping, or other adsorption methods.

The possible embodiments, the respective manufacturing processes, and the methods of incorporating the active substance may also be combined with one another in order to achieve certain properties.

For instance, the collagen preparation according to the present invention may comprise a shell of insoluble collagen with a low mean molecular weight, which is soluble or at least swellable in body fluid, in the form of a sponge or film containing a micro-particulate preparation of insoluble collagen having a high mean molecular weight dispersed therein. If only one active substance is incorporated, the outer sponge or film phase serves the quick release of active substance to achieve the required minimum active substance concentration very quickly, followed by a slower, more even release of active substance from the inner, particulate phase to maintain the required active substance concentration over the application period. Such release profiles may also be achieved with other preparation forms, such as fibers in hydrogels, spongy oil-in-water-emulsions, compressed mixtures for implantable tablets, multi-layer films, combinations of films and foams, and the like.

Such multi-phase preparations can also be used if a release of different active substances at different points of time with different release rates is desired, or if one or several active substances are to be released phase-like, i.e., with release-free intervals. In this case active substance A may, for example, be contained in a readily soluble, quick-releasing outer phase, whereas active substance B is contained in an inner phase which is slightly soluble and releases the active substances in a retarded and controlled sustained manner. If a phase-like release profile is desired for only one active substance, external and internal phase may, for example, release active substance at an even kinetics. However, the inner phase will then be surrounded by an active substance-free layer of insoluble collagen, which, after dissolution of the outer phase or active-substance-exhaustion thereof, must swell or dissolve itself first so that the active substance release from the inner phase can take place. By means of this arrangement, an interval without any active substance release can be obtained.

If the collagen preparation according to the present invention is used for the dermal, intradermal or transdermal application of pharmaceutical active substances or cosmetic active principles, plane embodiments, such as films, membranes, or thin sponges are preferred. These flat embodiments may consist of laminates which, for example, also include barrier layers which are free from active substances, permeable separating layers, controlling membranes, and adhesive layers. Substructures, such as laminae, powders, microparticles, or oil droplets, may then be introduced in or between the individual layers, in order to achieve the suitable release kinetics for one or several active substances. It is preferred that such single- or multi-layer collagen preparations for the mentioned applications, e.g., for protection against dehydration or growing in of germs, be provided with a backing layer and a removable protective layer located on the opposite side according to known processes, the backing layer and the protective layer consisting of materials known to the skilled artisan, for example, those used in the formulation of patches and adhesive tapes.

In a preferred embodiment of the collagen preparation according to the present invention for the use on external wounds and in the interior of the body, the preparation is paste-like, e.g., foamy or spongy. The size of the pores and the structure of the preparation are designed such that immigration of cells, e.g., fibroblasts or osteoblasts, into the preparation is possible and that the cells are given a structural orientation; this can particularly be attributed to the degree of orientation of the collagen in the preparation according to the present invention, which is similar to that of natural connective tissue. Immigration of the cells may be necessary, for example, for the degradation of the preparation or for the release or deposition of substances which are required, for example, for neo-formation of tissue or vascularization of a tissue which is to take the place of the collagen preparation according to the present invention.

In another preferred embodiment for the use on wounds or in the interior of the body, the collagen preparation according to the present invention is adjusted by admixing adjuvants, such as carboxymethylcellulose, polyacrylic acid, tragacanth, sodium alginate, or hydroxypropylcellulose in such a manner that it is bioadhesive, i.e., that it adheres to the surface tissue of the application site for a certain time by means of interfacial forces, in order to increase the retention time at the site of application or absorption.

EXAMPLES

1. Extraction of Insoluble Collagen from Calfskin

| 1.1 | Treatment with $Ca(OH)_2$ 1% in $H_2O$ | 100 h |
|---|---|---|
| | Treatment with $NH_4Cl$ 3% in $H_2O$ | 1 h |
| | Treatment with NaOH 5% + $Na_2SO_4$ 9.2% in $H_2O$ | 12 h |
| | Treatment with $Na_2SO_4$ 1 molar in $H_2O$ | 0.5 h |

-continued

| | |
|---|---|
| Treatment with HCl 1% in H$_2$O | 1.5 h |
| Treatment with H$_2$O$_2$ 0.5% in H$_2$O | 6 h |

After mechanical comminution and dispersion in H$_2$O (pH 6.0) the insoluble collagen has an average molecular weight of about 2,500,000. The collagen concentration amounts to 0.75%.

1.2 As in a), difference:

| | |
|---|---|
| Treatment with Ca(OH)$_2$ 1% in H$_2$O | 72 h |
| Treatment with NaOH 9.75% + Na$_2$ SO$_4$ 9.2% in H$_2$O | 48 h |

After mechanical comminution and dispersion in H$_2$O (pH 6.0) the insoluble collagen has an average molecular weight of about 420,000. The collagen concentration amounts to 0.75%.

2. Production of Active Substance-free Lyophilizates from Mixtures of the Dispersions According to 1.1 and 1.2 and Determination of the Disintegration Time in Buffer Mixtures having Different pH-values.

The following mixtures of the dispersions according to 1.1 and 1.2 were produced:

| | Dispersion 1.1 | Dispersion 1.2 |
|---|---|---|
| A | 100% | 0% |
| B | 75% | 25% |
| C | 50% | 50% |
| D | 25% | 75% |
| E | 0% | 100% |

24 g of the mixtures A to E were each filled into deep-drawing dies of 6×4×1.5 cm, shock-frozen and brought to a temperature of −50° C. within 60 minutes. Subsequently the mixtures were freeze-dried.

The disintegration time of the resulting sponges (dimensions 6×4×0.8 cm) was determined under slight stirring in 100 ml of the following buffer mixtures:

pH 3: buffer mixture citric acid/sodium chloride/sodium hydroxide solution with addition of a fungicide
pH 5: acetic acid (0.1 molar) sodium acetate (0.2 molar)
pH 6.4: artificial exudation of a wound (without albumin)
pH 7.5: potassium hydrogenphosphate/NaOH (0.1 molar/0.1 molar)

Results:

| | pH of buffer solution | | | |
|---|---|---|---|---|
| Mixture | 3 | 5 | 6.4 | 7.5 |
| A | 2 h 15 min | >10 d | >10 d | >10 d |
| B | 1 h 10 min | 3 d | 3 d | 2 d |
| C | 1 h | 24 h | 24 h | 6 h |
| D | 20 min | 4 h 10 min | 4 h 30 min | 1 h 45 min |
| E | 2 min | 35 min | 45 min | 15 min |

3. Production of Lyophilizates with p-Hydroxybenzoic Acid Propylester and Determination of the Release 0.275% (relative to the dispersion) of p-hydroxybenzoic acid propylester were dissolved in each of the mixtures A to E according to Example 2. 10 g of each of the mixtures were filled into deep-drawing dies according to Example 2, shock-frozen, cooled to −50° C. within 60 mins., and then freeze-dried.

About 30 mg (theoretical PHB-ester-content 6.1 mg) of each of the resulting lyophilizates (sponge weights about 135 mg, theoretical PHB-ester-content 27.5 mg) were placed in a paddle-device and stirred at 45 rpm in 500 ml of 0.05 N sodium hydroxide solution at 37° C. After 4 hours, 10 ml of each release medium were withdrawn. The active substance content was determined by ultraviolet-photometry against standard at 294 nm at a layer thickness of 1 cm.

Results:

| | Mixture | | | | |
|---|---|---|---|---|---|
| | A | B | C | D | E |
| released act. subst. (mg) | 2.1 | 2.7 | 3.4 | 3.8 | * |

* could not be determined because of complete disintegration of lyophilizate

4. Production of Lyophilizates with Lidocaine Hydrochloride and Determination of the Release 0.042% (relative to the dispersion) of lidocaine hydrochloride were dissolved in each of mixtures A to E according to Example 2. 24 g of each mixture were filled into deep-drawing dies according to Example 2, shock-frozen, cooled to −50° C. within 60 minutes, and then freeze-dried.

The resulting lyophilizates (sponge weights about 250 mg, theoretical content of lidocaine hydrochloride 10 mg) were each filled into a paddle-device and fixed at the bottom of the vessel by means of a net. 350 ml of water having a temperature of 37° C. were filled into the device and stirred at 45 rpm. After 24 hours, samples of the release medium were taken. The active substance content was determined at 262.5 nm and a layer thickness of 1 cm by means of ultraviolet-photometry and assessment based on a standard curve.

Results:

| Mixture | Active substance released |
|---|---|
| A | 1.2 mg |
| B | 5.1 mg |
| C | 7.4 mg |
| D | 8.8 mg |
| E | 10.0 mg |

What is claimed is:

1. A collagen preparation for the controlled release of active substance which comprises at least one active substance and a mixture of acid-insoluble collagen-fractions each fraction having a different mean molecular weight and said fractions being obtained by alkaline decomposition.

2. A collagen preparation according to claim 1, wherein the collagen preparation comprises a plurality of active substances.

3. A collagen preparation according to claim 1, comprising an adjuvant selected from the group consisting of viscosity, regulators, binders, humectants, softening agents, penetration enhancers, preservatives, disinfectants, pH-regulators, antioxidants, active substance stabilizers, oils, fats, waxes, emulsion stabilizers, odorous substances, dyes, inert fillers and mixtures thereof.

4. A collagen preparation according to claim 1, wherein the insoluble collagen is telopeptide-free, native, uncross-linked Type-1-collagen.

5. A collagen preparation according to claim 4, wherein the insoluble collagen is a product obtained from calfskin by alkaline decomposition.

6. A collagen preparation according to claim 1, in the form of powders, dusts, microparticles, fibers, flakes, foams, sponges, needles, rods, tablets, gels, creams, single-layer films, or laminates.

7. A collagen preparation according to claim 6, which comprises a combination of different forms of the collagen in order to obtain a desired kinetics of active substance release.

8. A collagen preparation according to claim 1, which is bioadhesive.

9. A process for the preparation of a collagen preparation according to claim 1, which comprises combining at least one active substance with a mixture of acid-insoluble collagen-fractions and subjecting such combination to spray drying, freeze-drying, coating or casting with subsequent drying, phase separation and coacervation processes, compression, or filling into containers.

10. A process according to claim 9, wherein the active substance release is controlled by the mixing ratio of acid-insoluble collagens having different mean molecular to weights.

11. A process according to claim 9, wherein the active substance release is controlled by dissolution or swelling and subsequent erosion of the collagen preparation.

12. A process according to claim 9, wherein the active substance release is controlled by the biodegradation of the collagen preparation.

13. A method for the treatment of a wound which comprises applying to the wound a collagen preparation as defined in claim 1.

14. A method for the use of a collagen preparation as defined in claim 1, which comprises applying said collagen preparation to intact skin.

15. A method for the use of a collagen preparation as defined in claim 1, which comprises implanting or injecting said collagen preparation into a living organism.

* * * * *